United States Patent [19]
Kopelowicz

[11] Patent Number: 5,873,364
[45] Date of Patent: Feb. 23, 1999

[54] LATEX PROPHYLACTICS

[76] Inventor: Alberto Kopelowicz, Calle 103, No. 1161/65, 1650 San Martin, Buenos Aires, Argentina

[21] Appl. No.: 795,424

[22] Filed: Feb. 5, 1997

Related U.S. Application Data

[63] Continuation of Ser. No. 685,463, Jul. 24, 1996, abandoned, which is a continuation of Ser. No. 604,225, Feb. 22, 1996, abandoned.

[51] Int. Cl.$^6$ ........................................................ A61F 6/02
[52] U.S. Cl. .......................... 128/842; 128/844; 128/918
[58] Field of Search ..................................... 128/842, 844, 128/918; 604/347–353; 600/38–42

[56] References Cited

U.S. PATENT DOCUMENTS

| | | | |
|---|---|---|---|
| 2,305,453 | 12/1942 | Martos | 128/844 |
| 2,586,674 | 2/1952 | Lonne | 128/844 |
| 4,895,140 | 1/1990 | Bellak | 600/39 |
| 5,176,152 | 1/1993 | Wheeler | 128/844 |
| 5,284,159 | 2/1994 | Wilk | 128/844 |
| 5,361,779 | 11/1994 | Wilson | 128/844 |
| 5,513,652 | 5/1996 | Schwartz | 128/842 |

OTHER PUBLICATIONS

V. G. Vokhmyanin, Soviet Patents Abstractsp. 3 section week 9505, Mar. 3, 1995. Derwent Publications Ltd. London.

*Primary Examiner*—Michael A. Brown
*Attorney, Agent, or Firm*—Kuhn and Muller

[57] ABSTRACT

A prophylactic includes a fabric layer reinforced by an inelastic weft extending in a longitudinal direction wherein the weft includes filaments woven with filaments of an elastic warp extending transversely, to allow the prophylactic to stretch without breaks and leaks.

2 Claims, 1 Drawing Sheet

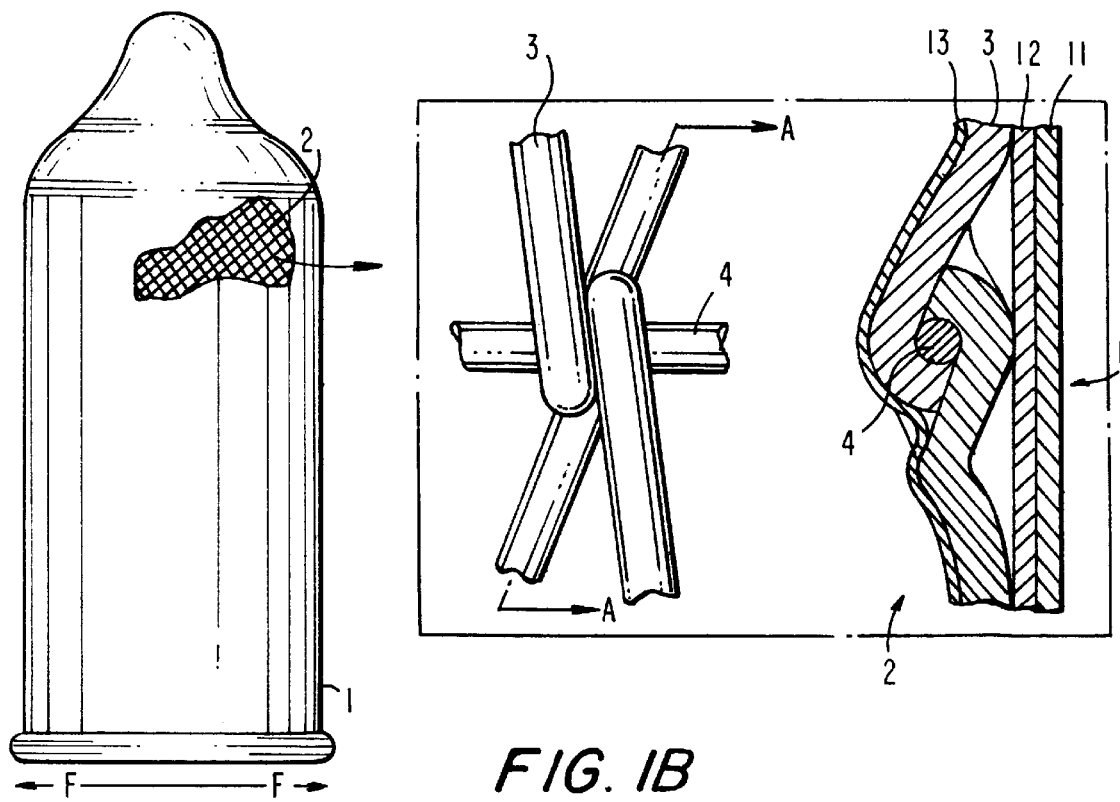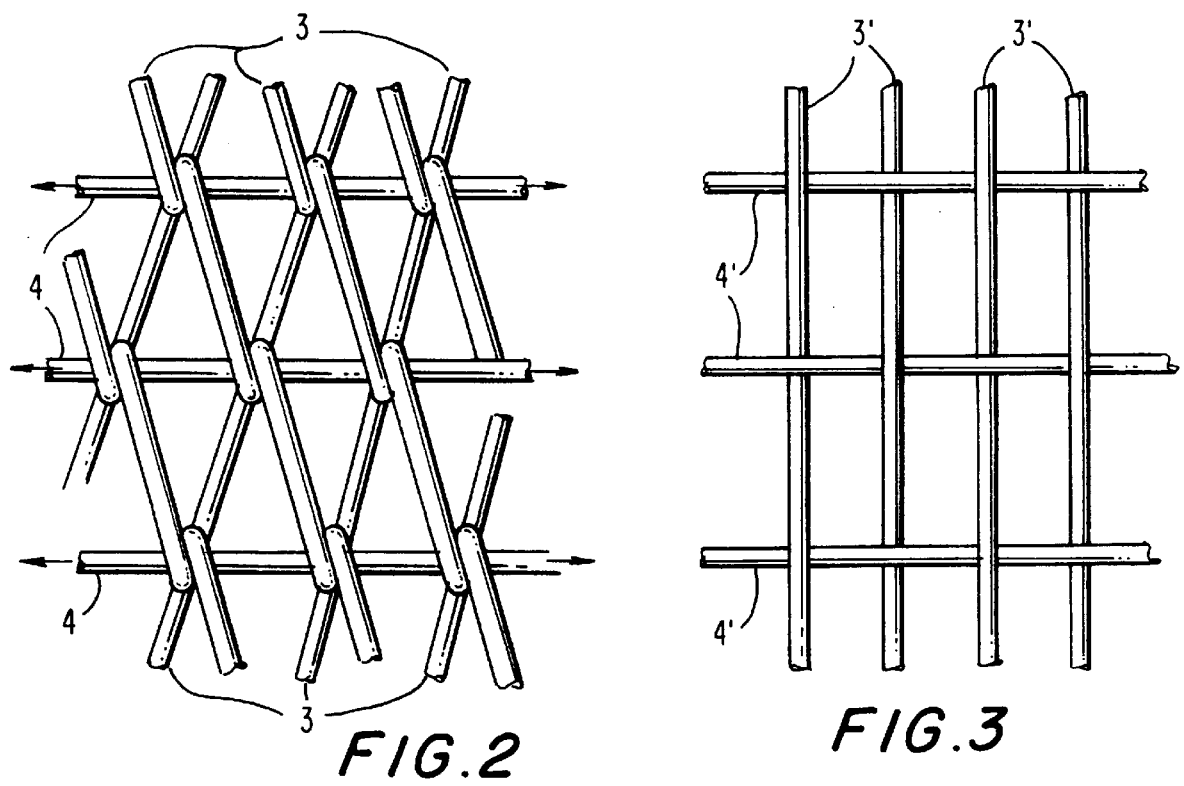

LATEX PROPHYLACTICS

This application is a continuation of Ser. No. 08/685,463 file Jul. 24, 1996, now abandoned, which is a continuation of Ser. No. 08/604,225 filed Feb. 22, 1996 now abandoned.

FIELD OF THE INVENTION

The present invention refers to improvements to latex prophylactics, which have a certain and constructive novel arrangement, wherein an increase in the resistance of the already known phophylactics is obtained. The construction of the prophylactic of the present invention increases its safety and efficiency, decreasing the risks of breakages, with the outstanding advantages of economic and practicality as noted in the details of the present specification.

BACKGROUND OF THE INVENTION

Known prophylactics or contraceptives are generally manufactured in latex or a similar elastomeric material in a form such that the prophylactics are conveniently used to cover the penis thereby avoiding the communication of the aqueous fluids in the act of sexual relations. As a consequence, the transmission of a plurality of sexually transmitted diseases that seriously risk the world population is reduced. When taking into consideration that contraceptive prophylactics are preferably manufactured in an elastomeric material of the latex type or the like, this presents the serious disadvantage of spontaneous breakage of the prophylactic, as well as, inconvenience due to its generally undesirable longitudinal stretching, so that its use becomes extremely risky due to the possibility of leakage or breakage in critical situations.

OBJECTS AND SUMMARY OF THE INVENTION

The undesirable effects of known prophylactics have been extremely surpassed and overcome with the prophylactics of the present invention. The novel features of the present invention, of which no prior antecedents are known, include the use of fabric incorporated in the manufacturing process of the contraceptive and include the incorporation of the fabric in the manufactured contraceptive. The incorporated fabric is shaped by the weaving of an inelastic weft in a longitudinal direction which is fastened to an elastic warp in a cross sectional sense, so as to allow the elasticity, adaptation and adjustment of the contraceptive in a transverse direction with respect to its central axis and an inelasticity in the longitudinal direction to the above mentioned axis so as not prejudice to its adaptability. This provides a total resistance to breakages and splits without affecting the adhesion or adaptability of the prophylactic and without requiring additional thickness in the walls of the contraceptive prophylactic, since the additional thickness may provoke irritation during use.

DESCRIPTION OF THE DRAWINGS

In order that the present invention be clearly understood and easily taken into operation, there has been submitted in one of its embodiments of a preferred form as noted in the illustrative drawings that accompany this specification in which:

FIG. 1 is a perspective view of the improved prophylactic of the present invention showing a close-up detail in elevation of the incorporated improvements of the weave of the prophylactic; its structural configuration and a warp and weft section, as shown through lines "A"—"A".

FIG. 2 is a close-up view of the incorporated fabric, showing the elastomeric filaments of the fabric and the elasticity of the fabric warp, and its elasticity in a sense direction and the rigid filaments of the weft interweaving on the above mentioned warp which are incorporated in the improvement illustrated in FIG. 1.

FIG. 3 shows an alternate embodiment for a variant of the improvement illustrated in FIG. 1, in the construction of which the elastomeric filaments of the warp, showing its expansion sense; as well as the inelastic longitudinal filaments of the waft, which are interweaved with the elastomeric filaments of the warp. The elastomeric filaments of the warp are shown in the expansion direction, as well as the inelastic longitudinal filaments that constitute the waft in the fabric of the improvement of the prophylactic of the present invention.

In said figures, the same reference figures indicate equal or similar parts.

DETAILED DESCRIPTION OF THE PREFERRED EMBODIMENTS

Now, having illustrated the improvement of the present invention there is shown the construction of the prophylactic (1). As shown in the close-up window detail view of FIG. 1, the prophylactic (1) includes incorporated fabric (2). Fabric (2) is constituted by a patterned weave consisting essentially of inelastic extremely thin filaments (3), which filaments (3) constitute the weft of the weave connected to extremely thin elastomeric filaments (4) that constitute the warp of the weave of the fabric (2) incorporated into the prophylactic (1). Fabric (2) is incorporated in the following manner: a base latex layer (11) is shaped on which a second layer (12) being also of latex is arranged (12). Once both layers (11) and (12) are consolidated and superposed, such as is illustrated in detail in FIG. 1, the fabric (2) base of the present improvement to the basic body of the prophylactic (1) is interpolated in solidarity with the body of the prophylactic (1) in an integral set, through a coating of the assembly with a lasting and extremely thin latex layer (13). The prophylactic (1) is finally shaped in definitive form in a simple and effective manner since the fabric (2) shaped by the weft (3) and the warp (4) is allowed to have an elastic adjustment of the improved unit in a radial direction to the axis of prophylactic (1), following a deformation in the direction illustrated by arrows f–f' thereby avoiding the stretching in the longitudinal direction of the prophylactic (1). This construction of prophylactic (1) with woven fabric (2) removes the possibilities of producing cracks in the prophylactic (1) or the breaking of same, since woven fabric (2) eliminates the longitudinal stretching, which longitudinal stretching is precisely the cause that most frequently produces same. Optionally, further layers may constitute a plurality of layers with layers (11), (12) and (13) of prophylactic (1).

It is hereby clarified that although the above mentioned construction of the prophylactic of the present invention is shown arranged a simple illustrative example, of the embodiments made therein, the fabric may be incorporated among any of the latex layers with which the prophylactic is manufactured, without same affecting the scope or essence of the present invention as noted in the appended claims.

I claim:

1. An improved latex prophylactic of a tubular body having an open distal end and a closed proximal end, comprising said prophylactic body having incorporated to the structure therein a fabric having a transversal warp and an inelastic longitudinal weft extending longitudinally in relation with an axis of said prophylactic.

2. The improved latex prophylactic as claimed in claim 1, wherein said fabric is interpolated between a plurality of latex layers within said prophylactic.

* * * * *